(12) United States Patent
    Yang

(10) Patent No.: US 11,174,312 B2
(45) Date of Patent: Nov. 16, 2021

(54) NAV1.9 TARGET POLYPEPTIDE, ANTIBODY AND ANTIBODY FRAGMENT COMBINED WITH SAME, AND RELATED PHARMACEUTICAL COMPOSITION

(71) Applicant: WUHAN UNIVERSITY, Wuhan (CN)

(72) Inventor: Daichang Yang, Wuhan (CN)

(73) Assignee: POPULAS BIOPHARMACEUTICAL (WUHAN) LIMITED, Wuhan (CN)

( * ) Notice: Subject to any disclaimer, the term of this patent is extended or adjusted under 35 U.S.C. 154(b) by 50 days.

(21) Appl. No.: 16/657,471

(22) Filed: Oct. 18, 2019

(65) Prior Publication Data

US 2020/0087393 A1    Mar. 19, 2020

Related U.S. Application Data

(63) Continuation of application No. PCT/CN2018/075597, filed on Feb. 7, 2018.

(51) Int. Cl.
    *C07K 16/28*    (2006.01)
    *C07K 16/18*    (2006.01)
    *A61K 39/395*   (2006.01)
    *A61P 29/02*    (2006.01)

(52) U.S. Cl.
    CPC .............. *C07K 16/28* (2013.01); *A61P 29/02* (2018.01); *C07K 2317/24* (2013.01); *C07K 2317/52* (2013.01); *C07K 2317/565* (2013.01)

(58) Field of Classification Search
    None
    See application file for complete search history.

(56) References Cited

FOREIGN PATENT DOCUMENTS

| CN | 102781963 A1 | 11/2012 |
|---|---|---|
| WO | 2011051351 A1 | 5/2011 |
| WO | 2018157710 A1 | 7/2018 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Leipold et al., "A de novo gain-of-function mutation in SCN11A causes loss of pain perception" Nature Genetics, 2013, v 45, n 11, p. 1399-1407.

* cited by examiner

*Primary Examiner* — Christine J Saoud
*Assistant Examiner* — Jon M Lockard
(74) *Attorney, Agent, or Firm* — Greer, Burns & Crain, Ltd.; Gregory P. Einhorn

(57) ABSTRACT

Provided is an antibody or a fragment thereof, which can be specifically bound to an S3-4 ring of a voltage sensor paddle of a domain III of voltage-gated sodium channel Nav1.9 α sub-unit, and is able to inactivate a voltage sensor valve to keep sodium ions from entering nerve cells normally. Also provided is an epitope polypeptide specifically bound to the antibody or the fragment thereof, a pharmaceutical composition comprising the antibody or the fragment thereof, and a use of the antibody or the fragment thereof in preparing a drug for treating and diseases related to pains.

8 Claims, 2 Drawing Sheets

Specification includes a Sequence Listing.

SEQUENCE LISTING

<160> NUMBER OF SEQ ID NOS: 13

<210> SEQ ID NO 1
<211> LENGTH: 5
<212> TYPE: PRT
<213> ORGANISM: Artificial
<220> FEATURE:
<223> OTHER INFORMATION: CDRH1

<400> SEQUENCE: 1

Ser Tyr Trp Met Asn
1               5

<210> SEQ ID NO 2
<211> LENGTH: 17
<212> TYPE: PRT
<213> ORGANISM: Artificial
<220> FEATURE:
<223> OTHER INFORMATION: CDRH2

<400> SEQUENCE: 2

Met Ile His Pro Ser Asp Ser Glu Thr Arg Leu Asn Gln Lys Phe Lys
1               5                   10                  15

Asp

<210> SEQ ID NO 3
<211> LENGTH: 5
<212> TYPE: PRT
<213> ORGANISM: Artificial
<220> FEATURE:
<223> OTHER INFORMATION: CDRH3

<400> SEQUENCE: 3

Gln Gly Phe Ala Tyr
1               5

<210> SEQ ID NO 4
<211> LENGTH: 11
<212> TYPE: PRT
<213> ORGANISM: Artificial
<220> FEATURE:
<223> OTHER INFORMATION: CDRL1

<400> SEQUENCE: 4

His Ala Ser Gln Asn Ile Asn Val Trp Leu Ser
1               5                   10

<210> SEQ ID NO 5
<211> LENGTH: 7
<212> TYPE: PRT
<213> ORGANISM: Artificial
<220> FEATURE:

<223> OTHER INFORMATION: CDRL2

<400> SEQUENCE: 5

Lys Ala Ser Asn Leu Arg Thr
1               5

<210> SEQ ID NO 6
<211> LENGTH: 9
<212> TYPE: PRT
<213> ORGANISM: Artificial
<220> FEATURE:
<223> OTHER INFORMATION: CDRL3

<400> SEQUENCE: 6

His Gln Gly Gln Ser Tyr Pro Trp Thr
1               5

<210> SEQ ID NO 7
<211> LENGTH: 469
<212> TYPE: PRT
<213> ORGANISM: Artificial
<220> FEATURE:
<223> OTHER INFORMATION: Heavy chain variable region

<400> SEQUENCE: 7

Met Gly Trp Ser Ser Ile Ile Leu Phe Leu Val Ala Thr Ala Thr Gly
1               5                   10                  15

Val His Ser Gln Val Gln Leu Gln Gln Pro Gly Ala Glu Leu Val Arg
                20                  25                  30

Pro Gly Ala Ser Val Lys Leu Ser Cys Lys Ala Ser Gly Tyr Ser Phe
            35                  40                  45

Thr Ser Tyr Trp Met Asn Trp Val Lys Gln Arg Pro Gly Gln Gly Leu
        50                  55                  60

Glu Trp Ile Gly Met Ile His Pro Ser Asp Ser Glu Thr Arg Leu Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Ala Arg Gln Gly Phe Ala Tyr Trp Gly Gln Gly Thr Leu
        115                 120                 125

Val Thr Val Ser Thr Ala Lys Thr Thr Pro Pro Ser Val Tyr Pro Leu
130                 135                 140

Ala Pro Gly Cys Gly Asp Thr Thr Gly Ser Ser Val Thr Leu Gly Cys
145                 150                 155                 160

Leu Val Lys Gly Tyr Phe Pro Glu Ser Val Thr Val Thr Trp Asn Ser
                165                 170                 175

Gly Ser Leu Ser Ser Ser Val His Thr Phe Pro Ala Leu Leu Gln Ser
            180                 185                 190

Gly Leu Tyr Thr Met Ser Ser Ser Val Thr Val Pro Ser Ser Thr Trp
        195                 200                 205

Pro Ser Gln Thr Val Thr Cys Ser Val Ala His Pro Ala Ser Ser Thr
    210                 215                 220

Thr Val Asp Lys Lys Leu Glu Pro Ser Gly Pro Ile Ser Thr Ile Asn
225                 230                 235                 240

Pro Cys Pro Pro Cys Lys Glu Cys His Lys Cys Pro Ala Pro Asn Leu
                245                 250                 255

Glu Gly Gly Pro Ser Val Phe Ile Phe Pro Pro Asn Ile Lys Asp Val

```
                    260                 265                 270
Leu Met Ile Ser Leu Thr Pro Lys Val Thr Cys Val Val Asp Val
                275                 280                 285
Ser Glu Asp Asp Pro Asp Val Gln Ile Ser Trp Phe Val Asn Asn Val
            290                 295                 300
Glu Val His Thr Ala Gln Thr Gln Thr His Arg Glu Asp Tyr Asn Ser
305                 310                 315                 320
Thr Ile Arg Val Val Ser Thr Leu Pro Ile Gln His Gln Asp Trp Met
                325                 330                 335
Ser Gly Lys Glu Phe Lys Cys Lys Val Asn Asn Lys Asp Leu Pro Ser
                340                 345                 350
Pro Ile Glu Arg Thr Ile Ser Lys Ile Lys Gly Leu Val Arg Ala Pro
                355                 360                 365
Gln Val Tyr Ile Leu Pro Pro Ala Glu Gln Leu Ser Arg Lys Asp
    370                 375                 380
Val Ser Leu Thr Cys Leu Val Val Gly Phe Asn Pro Gly Asp Ile Ser
385                 390                 395                 400
Val Glu Trp Thr Ser Asn Gly His Thr Glu Glu Asn Tyr Lys Asp Thr
                405                 410                 415
Ala Pro Val Leu Asp Ser Asp Gly Ser Tyr Phe Ile Tyr Ser Lys Leu
                420                 425                 430
Asn Met Lys Thr Ser Lys Trp Glu Lys Thr Asp Ser Phe Ser Cys Asn
                435                 440                 445
Val Arg His Glu Gly Leu Lys Asn Tyr Tyr Leu Lys Lys Thr Ile Ser
    450                 455                 460
Arg Ser Pro Gly Lys
465

<210> SEQ ID NO 8
<211> LENGTH: 234
<212> TYPE: PRT
<213> ORGANISM: Artificial
<220> FEATURE:
<223> OTHER INFORMATION: Light chain variable region

<400> SEQUENCE: 8

Met Arg Val Leu Ala Glu Leu Leu Gly Leu Leu Leu Phe Cys Phe Leu
1               5                   10                  15
Gly Val Arg Cys Asp Ile Gln Met Asn Gln Ser Pro Ser Ser Leu Ser
            20                  25                  30
Ala Ser Leu Gly Asp Thr Ile Thr Ile Thr Cys His Ala Ser Gln Asn
        35                  40                  45
Ile Asn Val Trp Leu Ser Trp Tyr Gln Gln Lys Pro Gly Asn Ile Pro
    50                  55                  60
Lys Leu Leu Ile Tyr Lys Ala Ser Asn Leu Arg Thr Gly Val Pro Ser
65                  70                  75                  80
Arg Phe Ser Gly Ser Gly Ser Gly Thr Gly Phe Thr Leu Thr Ile Ser
                85                  90                  95
Ser Leu Gln Pro Glu Asp Ile Ala Thr Tyr Tyr Cys His Gln Gly Gln
            100                 105                 110
Ser Tyr Pro Trp Thr Phe Gly Gly Gly Thr Lys Leu Glu Ile Lys Arg
        115                 120                 125
Ala Asp Ala Ala Pro Thr Val Ser Ile Phe Pro Pro Ser Ser Glu Gln
    130                 135                 140
Leu Thr Ser Gly Gly Ala Ser Val Val Cys Phe Leu Asn Asn Phe Tyr
```

145                 150                 155                 160
Pro Lys Asp Ile Asn Val Lys Trp Lys Ile Asp Gly Ser Glu Arg Gln
                165                 170                 175
Asn Gly Val Leu Asn Ser Trp Thr Asp Gln Asp Ser Lys Asp Ser Thr
                180                 185                 190
Tyr Ser Met Ser Ser Thr Leu Thr Leu Thr Lys Asp Glu Tyr Glu Arg
                195                 200                 205
His Asn Ser Tyr Thr Cys Glu Ala Thr His Lys Thr Ser Thr Ser Pro
                210                 215                 220
Ile Val Lys Ser Phe Asn Arg Asn Glu Cys
225                 230

<210> SEQ ID NO 9
<211> LENGTH: 14
<212> TYPE: PRT
<213> ORGANISM: Artificial
<220> FEATURE:
<223> OTHER INFORMATION: Polypeptide specifically binding to antibody

<400> SEQUENCE: 9

Asp Val Glu Phe Ser Gly Glu Asp Asn Ala Gln Arg Ile Thr
1               5                   10

<210> SEQ ID NO 10
<211> LENGTH: 1410
<212> TYPE: DNA
<213> ORGANISM: Artificial
<220> FEATURE:
<223> OTHER INFORMATION: DNA sequence of heavy chain variable region

<400> SEQUENCE: 10

```
atgggatgga gctctatcat cctcttcttg gtagcaacag ctacaggtgt ccactcccag      60
gtccaactgc agcagcctgg ggctgagctg gtgaggcctg agcttcagt gaagctgtcc     120
tgcaaggctt ctggctactc cttcaccagt tactggatga actgggtgaa gcagaggcct     180
ggacaaggcc ttgagtggat tggcatgatt catccttccg atagtgaaac taggttaaat     240
cagaagttca aggacaaggc acattgact gtagacaaat cctccagcac agcctacatg      300
caactcagca gcccgacatc tgaggactct gcggtctatt actgtgcaag acaagggttt     360
gcttactggg gccaagggac tctggtcact gtctctacag ccaaaacaac ccccatca       420
gtctatccac tggcccctgg gtgtggagat acaactggtt cctccgtgac tctgggatgc     480
ctggtcaagg gctacttccc tgagtcagtg actgtgactt ggaactctgg atccctgtcc    540
agcagtgtgc acaccttccc agctctcctg cagtctggac tctacactat gagcagctca     600
gtgactgtcc cctccagcac ctggccaagt cagaccgtca cctgcagcgt tgctcaccca     660
gccagcagca ccacggtgga caaaaaactt gagcccagcg ggcccatttc aacaatcaac     720
ccctgtcctc catgcaagga gtgtcacaaa tgcccagctc ctaacctcga gggtggacca     780
tccgtcttca tcttccctcc aaatatcaag gatgtactca tgatctccct gacacccaag     840
gtcacgtgtg tggtggtgga tgtgagcgag gatgacccag acgtccagat cagctggttt     900
gtgaacaacg tggaagtaca cacagctcag acacaaaccc atagagagga ttacaacagt     960
actatccggg tggtcagcac cctccccatc agcaccagg actggatgag tggcaaggag    1020
ttcaaatgca aggtcaacaa caaagacctc ccatcaccca tcgagagaac catctcaaaa   1080
attaaagggc tagtcagagc tccacaagta tacatcttgc cgccaccagc agagcagttg   1140
tccaggaaag atgtcagtct cacttgcctg gtcgtgggct tcaaccctgg agacatcagt   1200
```

```
gtggagtggga ccagcaatgg gcatacagag gagaactaca aggacaccgc accagtcctg    1260
gactctgacg gttcttactt catatatagc aagctcaata tgaaaacaag caagtgggag    1320
aaaacagatt ccttctcatg caacgtgaga cacgagggtc tgaaaaatta ctacctgaag    1380
aagaccatct cccggtctcc gggtaaatga                                      1410

<210> SEQ ID NO 11
<211> LENGTH: 705
<212> TYPE: DNA
<213> ORGANISM: Artificial
<220> FEATURE:
<223> OTHER INFORMATION: DNA sequence of light chain variable region

<400> SEQUENCE: 11
atgagggtcc ttgctgagct cctggggctg ctgctgttct gcttttagg tgtgagatgt      60 gacatccaga tgaaccagtc tccatccagt ctgtctgcat cccttggaga cacaattacc    120
atcacttgcc atgccagtca gaacattaat gtttggttaa gctggtacca gcagaaacca    180
ggaaatattc ctaaactatt gatctataag gcttccaact tgcgcacagg cgtcccatca    240
aggtttagtg gcagtggatc tggaacaggt ttcacattaa ccatcagcag cctgcagcct    300
gaagacattg ccacttacta ctgtcaccag ggtcaaagtt atccgtggac gttcggtgga    360
ggcaccaagc tggaaatcaa acgggctgat gctgcaccaa ctgtatccat cttcccacca    420
tccagtgagc agttaacatc tggaggtgcc tcagtcgtgt gcttcttgaa caacttctac    480
cccaaagaca tcaatgtcaa gtggaagatt gatggcagtg aacgacaaaa tggcgtcctg    540
aacagttgga ctgatcagga cagcaaagac agcacctaca gcatgagcag caccctcacg    600
ttgaccaagg acgagtatga cgacataac agctatacct gtgaggccac tcacaagaca    660
tcaacttcac ccattgtcaa gagcttcaac aggaatgagt gttag                    705

<210> SEQ ID NO 12
<211> LENGTH: 1410
<212> TYPE: RNA
<213> ORGANISM: Artificial
<220> FEATURE:
<223> OTHER INFORMATION: RNA sequence of heavy chain variable region

<400> SEQUENCE: 12
augggaugga gcucuaucau ccucuucuug guagcaacag cuacaggugu ccacucccag     60
guccaacugc agcagccugg ggcugagcug gugaggccug agcuucagu gaagcugucc    120 ugcaaggcuu cuggcuacuc cuucaccagu uacuggauga cuggguggaa gcagaggccu   180
ggacaaggcc uugaguggau uggcaugauu caucuuccg auagugaaac uagguuaaau    240
cagaaguuca aggacaaggc cacauugacu guagacaaau ccuccagcac agccuacaug    300
caacucagca gcccgacauc ugaggacucu gcggucuauu acugugcaag acaagggguuu   360 gcuuacuggg gccaagggac ucuggucacu gucucuacag ccaaaacaac cccccauca    420 gucuauccac uggcccuggg gugugagau acaacugguu ccuccgugac ucugggaugc    480
cuggucaagg cuacuucccc ugagucagug acugugacuu ggaacucugg auccccugcc    540
agcagugugc acaccuuccc agcucuccug cagucuggac ucuacacuau gagcagcuca    600
gugacugucc ccuccagcac cuggccaagu cagaccgcuca ccugcagcgu ugcuacccca   660
gccagcagca ccacgguggga caaaaacuu gaccagcg ggcccauuuc aacaaucaac     720 cccugucccuc caugcaagga gugucacaaa ugcccagcuc cuaaccucga gguggacca    780
```

```
uccgucuuca ucuucccucc aaauaucaag gauguacuca ugaucucccu gacacccaag      840
gucacgugug uggugguggga ugugagcgag gaugacccag acguccagau cagcugguuu      900
gugaacaacg uggaaguaca cacagcucag acacaaaccc auagagagga uuacaacagu      960
acuauccggg uggucagcac ccucccccauc cagcaccagg acuggaugag uggcaaggag     1020
uucaaaugca aggucaacaa caaagaccuc ccaucaccca ucgagagaac caucucaaaa     1080
auuaaagggc uagucagagc uccacaagua uacaucuugc cgccaccagc agagcaguug     1140
uccaggaaag augucagucu cacuugccug gucgugggcu ucaacccugg agacaucagu     1200 gguggagugga ccagcaaugg gcauacagag gagaacuaca aggacaccgc accaguccug     1260
gacucugacg guucuuacuu cauauauagc aagcucaaua ugaaaacaag caagugggag     1320
aaaacagauu ccuucucaug caacgugaga cacgaggguc ugaaaaauua cuaccugaag     1380
aagaccaucu cccggucucc ggguaaauga                                      1410

<210> SEQ ID NO 13
<211> LENGTH: 705
<212> TYPE: RNA
<213> ORGANISM: Artificial
<220> FEATURE:
<223> OTHER INFORMATION: RNA sequence of light chain variable region

<400> SEQUENCE: 13 auggggucc uugcugagcu ccuggggcug cugcuguucu gcuuuuuagg ugugagaugu       60
gacauccaga ugaaccaguc uccauccagu cugucugcau cccuuggaga cacaauuacc      120
aucacuugcc augccaguca gaacauuaau guuugguuaa gcugguacca gcagaaacca      180
ggaaauauuc cuaaacuauu gaucuauaag gcuuccaacu ugcgcacagg cgucccauca      240
agguuuagug gcagguggauc uggaacaggu uucacauuaa ccaucagcag ccugcagccu      300
gaagacauug ccacuuacua cugucaccag ggucaaaguu auccgguggac guucggugga      360 ggcaccaagc uggaaaucaa acgggcugau gcugcaccaa cuguauccau cuucccacca      420
uccagugagc aguuaacauc uggaggugcc ucagucgugu gcuucuugaa caacuucuac      480
cccaaagaca ucaaugucaa guggaagauu gauggcagug aacgacaaaa uggcguccug      540
aacaguugga cugaucagga cagcaaagac agcaccuaca gcaugagcag cacccucacg      600
uugaccaagg acgaguauga acgacauaac agcuauaccu gugaggccac ucacaagaca      660
ucaacuucac ccauugucaa gagcuucaac aggaaugagu guuag                     705
```

NAV1.9 TARGET POLYPEPTIDE, ANTIBODY AND ANTIBODY FRAGMENT COMBINED WITH SAME, AND RELATED PHARMACEUTICAL COMPOSITION

RELATED APPLICATIONS

This U.S. utility patent application is a continuation of PCT International Application PCT/CN2018/075597, filed Feb. 7, 2018, which claims benefit of priority to Chinese Patent Application No. 201710124693.9, filed Mar. 3, 2017, now expired. The aforementioned applications are expressly incorporated herein by reference in their entirety and for all purposes.

FIELD OF THE INVENTION

The present invention relates to a Nav1.9 target (polypeptide), an antibody and/or antibody fragment which specifically recognize the above target (polypeptide or Nav 1.9 channel), and a pharmaceutical composition comprising the above antibody and/or antibody fragment for treatment of pains, itching and cough.

BACKGROUND OF THE INVENTION

Pain begins with the nociceptors of the peripheral nervous system that are widely distributed in the skin, muscles, joints and visceral tissues of the whole body as a kind of free nerve endings, and can convert thermal, mechanical or chemical stimuli into action potentials, transmit them to the cell body in the dorsal root ganglia (DRG) through the nerve fibers and ultimately to the advanced nerve center, thereby causing pains. The generation and conduction of action potentials in neurons in turn depend on the voltage-gated sodium channels (VGSCs) located on the cytomembrane. When the cytomembrane is depolarized, the sodium ion channel is activated. The channel is opened, causing sodium ion influx, and further depolarizing the cytomembrane, resulting in the generation of an action potential, and thus causing pain due to the abnormal action potential. Therefore, inhibition of abnormal sodium ion channel activity contributes to the treatment and alleviation of pain.

Figure 1:
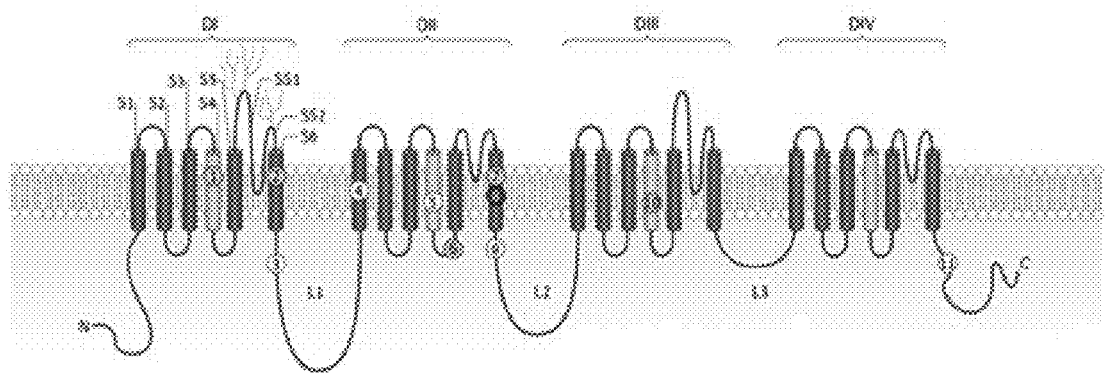

Voltage-gated sodium ion channels are widely found on the cytomembranes of neuron and skeletal muscle cells, which are a class of transmembrane glycoprotein complexes composed of an α subunit and several β subunits. The α subunit is a functional carrier of sodium ion channels, consisting of 1700 to 2000 amino acids, forming 4 domains (I-IV), each of which contains 6 transmembrane segments (S1-S6) (FIG. 1). The domains are connected by some large intracellular loops, and the fragments are connected by small extracellular or intracellular loops. Among them, S4 is rich in basic amino acid residues and is considered to be a voltage-sensitive component of voltage-gated sodium ion channels. When the cytomembrane is depolarized, the positive charges on S4 can move out along the axis of S4 in a clockwise direction, change the sodium ion channel conformation and make the channel open. The pore loop (P-loop) between S5 and S6 forms the extracellular portion of the micropore, which is related to the selectivity to sodium ions, while the intracellular portion of the micropore is surrounded by S6. The intracellular loop linking domains III and IV acts as an inactivation valve that can fold into the intracellular opening of the micropore, block the micropore, and inactivate the voltage-gated sodium ion channel Mutations in the L2 intimal region of domain II can result in a pain-free phenotype (Nature Genetics, 2013, 45 (11): 1399-1404).

It can be classified according to differences, nine voltage-gated sodium ion channel α subunits have been identified in mammals so far, since the amino acid sequences have more than 50% similarity, they are considered to be from the same family, named Nav1 (Nav1.1-Nav1.9). Experiments have shown that they are expressed in large amounts in neurons, and Nav1.9 is present in the peripheral nervous system (PNS). Recent studies have shown that the subtypes of Nav1 associated with pain are mainly Nav1.3, Nav1.7, Nav1.8 and Nav1.9. Nav1.9 is an important member mainly responsible for pain. Nav1.9 is a TTX-R type having the coding gene of SCN11A and is mainly distributed in the DRG neurons, trigeminal ganglia and intestinal myenteric neurons for feeling hurt. The activation voltage of Nav1.9 is close to the resting membrane potential of neurons (−60~−70 mV), with a dynamic characteristic of slow activation and slow deactivation, so it can produce a longer-lasting TTX-R current, which indicates that Nav1 0.9 can amplify and prolong the response of neurons to subthreshold depolarization, and trigger an action potential. In the human body, the activation voltage of Nav1.9 is −80 mV. Recently, in the pain-free patients, the amino acid mutation at position 811 in Nav1.9 has produced painless symptoms. Further research on the gene indicates that the gene is one of the sodium ion channels mainly responsible for pain.

Chemical small molecules (such as carbamazepine, lidocaine, mexiletine, etc.) are generally used in clinical as a voltage-gated sodium ion channel inhibitor for the treatment of pain. However, due to lacking of sufficient selectivity for voltage-gated sodium ion channel subtypes, they have the shortcoming of producing cardiotoxicity and central nervous side effects.

SUMMARY OF THE INVENTION

The first object of the present invention is to provide a voltage sensor paddle region of domain III in Nav1.9 as a target, using the target in such region to design a polypeptide as an antigen, to obtain a monoclonal antibody. By binding the specific antibody to its target, the VGSCs ion channel can be closed, thereby inhibiting pain. The polypeptide has the sequence as shown in SEQ ID NO:9, or a structurally similar derivative sequence having 80%, 80~85%, 85~90%, 90~95% or 95~99% homology to the polypeptide.

The second object of the present invention is to provide an antibody and antibody fragment thereof that specifically recognize the target, comprising a heavy chain variable region (VH) having the sequence as shown in SEQ ID NO:7 or a structurally similar derivative sequence with 80%, 80~85%, 85~90%, 90~95% or 95~99% homology to the sequence as shown in SEQ ID NO:7; and a light chain variable region (VL) having the sequence as shown in SEQ ID NO:8 or a structurally similar derivative sequence with 80%, 80~85%, 85~90%, 90~95% or 95~99% homology to the sequence as shown in SEQ ID NO:8; Also, the three CDR sequences contained in the heavy chain variable region (SEQ ID NO:7) and/or the three CDR sequences contained in light chain variable region (SEQ ID NO:8) can be optimized, to obtain a CDR chimeric antibody and antibody fragment thereof. The CDR sequences contained in the heavy chain variable region comprise CDRH1 as shown in SEQ ID NO.1, CDRH2 as shown in SEQ ID NO.2, and CDRH3 as shown in SEQ ID NO.3; the CDR sequences contained in the light variable region comprise CDRL1 as shown in SEQ ID NO.7, CDRL2 as shown in SEQ ID NO.5, and CDRL3 as shown in SEQ ID NO.6.

The light chain constant region of the antibody and antibody fragment thereof may be selected from a κ chain or a λ chain, and the heavy chain constant region thereof may be selected from the group consisting of IgM, IgD, IgG 1-4, IgA, IgE, etc.

The species sources of the light chain constant region and the heavy chain constant region may be selected from the group consisting of human antibody constant region, bovine antibody constant region, sheep antibody constant region, canine antibody constant region, porcine antibody constant region, feline antibody constant region, equine antibody constant region, and scorpion antibody constant region.

The antibody and antibody fragment thereof may be in a structural form selected from the group consisting of a full antibody, Fab, F(ab')2, dsFv, scFv, a diabody, a minibody, a bispecific antibody, a multispecific antibody, a chimeric antibody, a CDR-graft antibody.

The antibody and antibody fragment thereof are preferably a monoclonal antibody or antibody fragment.

More preferably, the antibody is a humanized monoclonal antibody.

The third object of the present invention is to provide a pharmaceutical composition comprising the above antibody or antibody fragment thereof as an active ingredient. The pharmaceutical composition has an analgesic effect and an effect of increasing pain threshold, and can treat pains, itching and cough.

According to the first aspect of the invention, based on the crystal structural model of Nav1.9, in the voltage sensor paddle region of domain III of the voltage sensor valve of Nav1.9, a polypeptide suitable for the target region is screened as an antigen. Through hydrophilicity and antigenicity analysis, a polypeptide with good hydrophilicity and high antigenicity is screened, having the amino acid sequence of DVEFSGEDNAQRIT (SEQ ID NO.9).

According to the second aspect of the invention, the first step is to prepare a monoclonal cell line that secrets the antibody.

The above polypeptide is chemically synthesized and designated as C2363BB030-1 (SEQ ID NO. 9), which is coupled to the carrier protein KLH, and then immunized to BALB/c mice, and multiple immunizations are used to stimulate the body to generate an immune response to produce polyclonal antibodies, for blood tests, ELISA tests and evaluations.

The polyclonal antibody titer produced by the immunized animal was evaluated by ELISA through antigen-antibody reaction. Based on the antibody titer of the immunized animal and the specificity of human neural tissues, two animals #1942, #1943 that met the requirements are finally determined for cell fusion. The spleen cells of the two animals are electrofused with mouse myeloma cells (SP2/0), and then cultured after fusion, and the positive cell lines are screened on the screening medium. The titer and tissue specificity of the secreted antibody are tested, and the hybridoma cell lines are screened using the polypeptide C2363BB030-1 as an antigen. According to the ELISA test results, positive cell lines are selected for subcloning. After the obtained subclones are subjected to ELISA test and specificity test again, the ones specific and positive for nerve tissues are selected and cryopreserved.

The second step is to sequence the variable region of the native antibody, comprising extracting the total RNA of the cell line, synthesizing the cDNA, establishing a cDNA library, and sequencing the variable region. Amplification of a polynucleotide sequence encoding a variable region of an antibody, which may comprise integrating DNA sequences encoding VH and VL (which may also be manipulated by RNA sequences encoding variable regions) into the same vector, or integrating them into vectors, respectively, and transfecting a suitable host cell with the above vector; and then subjecting it to sequencing analysis. The sequencing results show that the DNA sequence of the VH is as shown in SEQ ID NO:10, and the DNA sequence of the VL is as shown in SEQ ID NO:11.

The third step is to construct a genetically engineered antibody by introducing the above DNA sequences encoding VH and VL (or encoding the CDR in VH and encoding the CDR in VL) into a suitable host for antibody expression according to different needs, and verifying the antibody effect.

Figure 4:
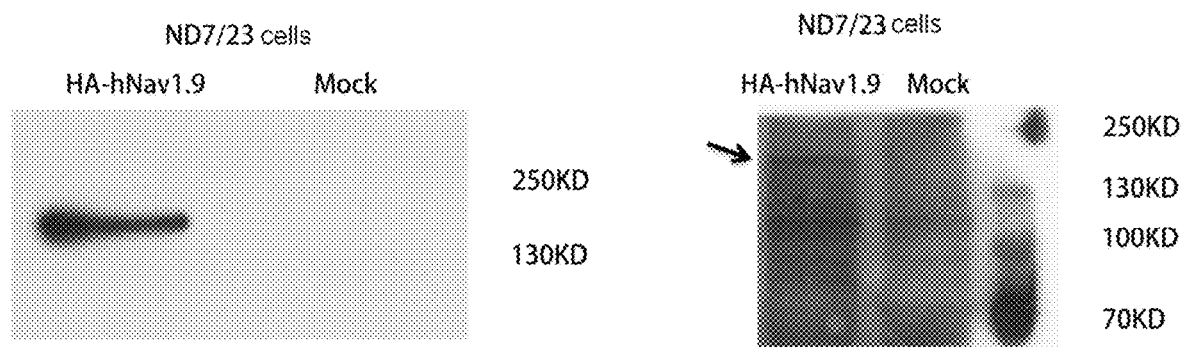

The third aspect of the present invention is to detect the biological activity of the monoclonal antibody. First, the human Nav1.9 gene is transiently expressed in ND7/23 cells, and the total protein is extracted from the transiently expressed ND7/23 cell line. The specificity of the antibody binding is analyzed by Western Blotting. As shown in FIG. 4, the antibody specifically recognizes the Nav1.9 protein.

Figure 5:
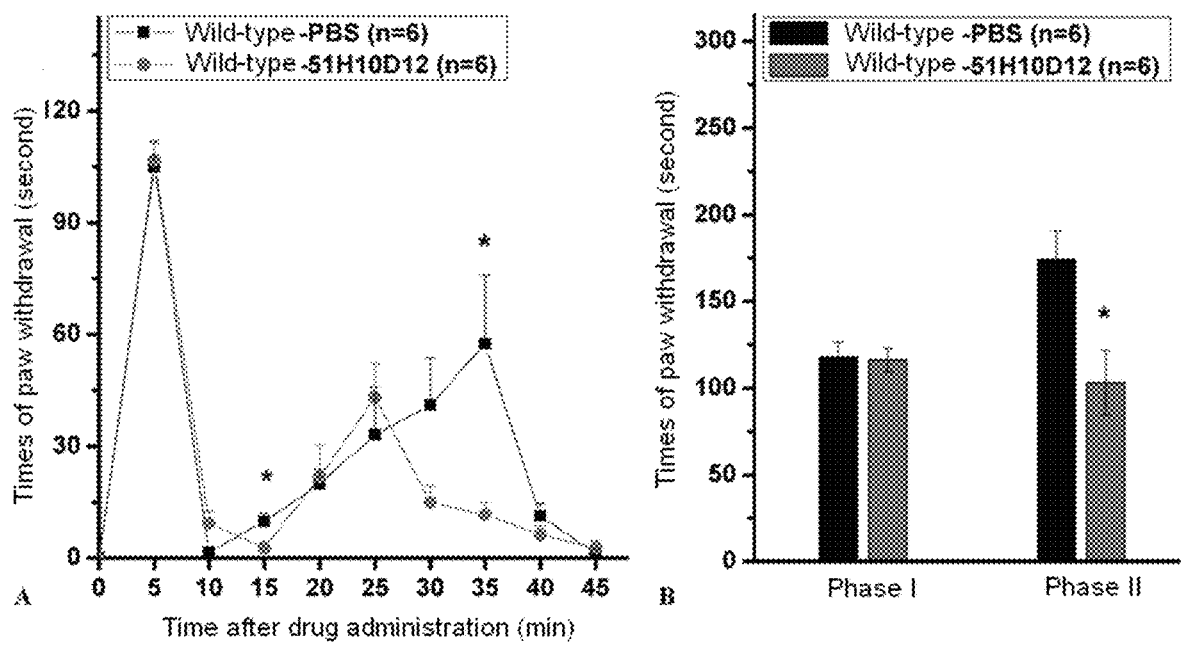

The second step is to establish an acute inflammatory pain model induced by 5% Formalin in mice. An appropriate amount of antibody is injected into the tail vein to detect the analgesic effect of the antibody on mice model with pain. The results are shown in FIG. 5, the analgesic effect after injection of 10 mg/kg of antibody is more significant compared to the control.

Beneficial effects: The targeted specific binding of the biomacromolecules such as antibody to the voltage sensor of the voltage-gated sodium ion channel Nav1.9 is used to inactivate the voltage sensor valve to keep sodium ions from entering nerve cells normally, thereby achieving the effect of treating and relieving pains. Due to their good targeting, they can overcome the side effects caused by chemical small molecule drugs.

DESCRIPTION OF THE INVENTION

FIG. 1: Structure diagram of the sodium ion channel Nav1.9

Figure 2:
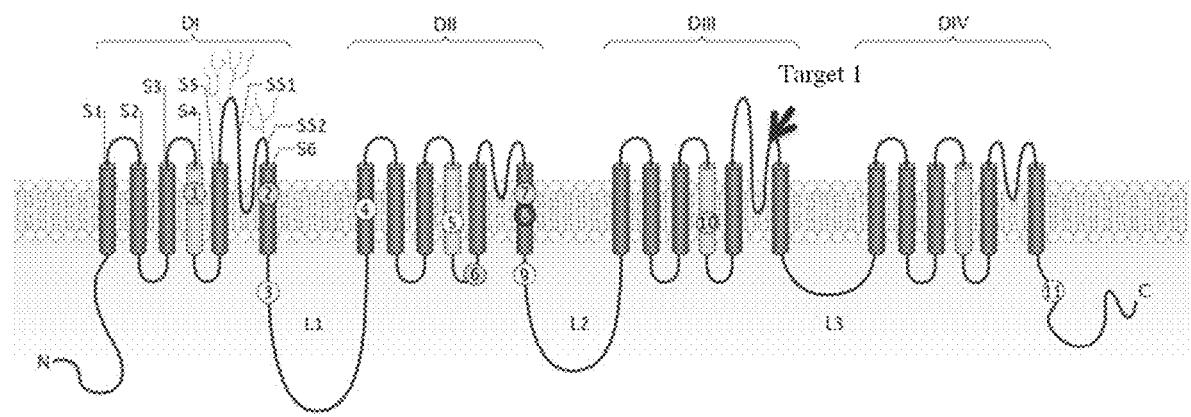

FIG. 2: Target design diagram of the sodium ion channel Nav1.9

Figure 3:
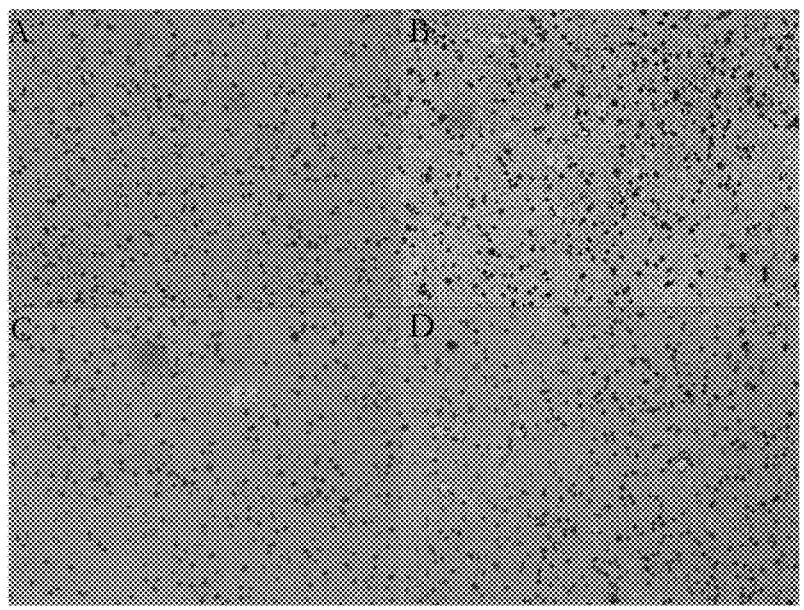

FIG. 3: Analysis of specificity of monoclonal antibodies to human neural tissues
A. 42H10; B. 51H10; C. 52F11; D. 55E9

FIG. 4: Immunogenicity analysis of monoclonal antibodies by Western blotting

FIG. 5: Analgesic effect of antibody 51H10D12 on 5% Formalin-induced acute inflammatory pain model in wild type mice.

DETAILED DESCRIPTION OF THE INVENTION

The invention is illustrated, but not limited by the following detailed description of the preferred embodiments of the invention.

Material Sources:

The materials and reagents used below are commercially available unless otherwise stated.

Example 1 [Synthesis of Antigen]

According to the amino acid sequence (GenBank No. NP_001274152) and the crystal structural model of Nav1.9, the hydrophilicity and antigenicity analyses were performed to screen the sequence DVEFSGEDNAQRIT, the hydrophilicity and antigenicity of which met the requirements of the antigen. The DVEFSGEDNAQRIT (SEQ ID NO.9) polypeptide was synthesized using a fully automated synthesizer.

Specific steps were as follows:

(1) attaching —COOH of the first AA to Cl-Resin with DIEA, and then blocking the unreacted functional groups on the resin with MeOH;

(2) washing with DMF;

(3) removing the protecting group Fmoc of —NH$_2$ in the first AA with Pip to expose the —NH$_2$;

(4) washing with DMF;

(5) activating —COOH of the second AA with DIC+HOBT, and then condensing it with —NH$_2$ in the first AA to form an amide bond;

(6) washing with DMF;

(7) removing the protecting group Fmoc of —NH$_2$ in the second AA with Pip to expose the —NH$_2$;

(8) washing with DMF;

(9) . . . repeating the steps 5-8 until exposing the —NH$_2$ of the last AA;

(10) cutting the polypeptide from the resin and removing the side chain protecting groups of all amino acids, with the cleavage reagent as: trifluoroacetic acid+ethanedithiol+phenol+thioanisole+water;

(11) adding the cleavage solution into diethyl ether to precipitate the polypeptide, and centrifuging to obtain the crude peptide (C2363BB030-1);

(12) purifying with a peptide HPLC C18 preparative/analytical column, designated as C2363BB030-1, to obtain the purified polypeptide for immunizing animals.

Note: To facilitate peptide coupling, an additional cysteine may be added to the end of the polypeptide.

Example 2 [Preparation of Monoclonal Cell Lines]

2.1 Animal Immunization

Freund's complete adjuvant (Sigma, F5881) and Freund's incomplete adjuvant (Sigma, F5506) were prepared. The polypeptide was coupled to the carrier protein KLH by the terminal —SH of polypeptide C2363BB030-1 and used as an immunogen.

Five 8-week-old female BALB/c mice (animal numbers: #1939, #1940, #1941, #1942, #1943) were selected and immunized intraperitoneally three times to stimulate the body to produce an immune response and then to produce antibodies. Primary immunization: 50 μg/mouse; the secondary immunization was performed after three weeks, at a dose of 50 μg/mouse; the third immunization was carried out 2 weeks after the secondary immunization at a dose of 50 μg/mouse; 1 week after the third immunization, blood was collected for antibody test.

2.2 ELISA Test of Animal Serum 2.2.1 Instruments and Equipments:
Washing machine: Beijing Nanhua ZDMX
Microtiter-plate reader: Thermo MultiskanAscent 2.2.2 Reagents:
Coating antigen: polypeptide C2363BB030-1; coating solution: 1*PBS (pH 7.4); washing buffer: 1*PBS (pH 7.4), 0.05% PBS; primary antibody: anti-serum after the third immunization; enzyme-labeled secondary antibody: Peroxidase-AffiniPure Goat Anti-Mouse IgG, Fcγ Fragment Specific (min X Hu, Bov, HrsSr Prot); TMB chromogenic solution; stop solution: 1 M hydrochloric acid.

The specific method was as follows:

(1) Coating: The antigen was diluted to 1 μg/ml with the coating solution, mixed and then added to the plate at 100 μl per well, covered with the cover film, and placed at 4° C. overnight.

(2) Blocking: The microtiter-plate was taken out to discard the coating solution, added with the blocking solution, covered with the cover film, and incubated at 37° C. for 0.5 h.

(3) Addition of primary antibody: The anti-serum after the third immunization was first diluted 1000-fold, and then subjected to doubling dilution for 9 gradients, covered with the cover film, and incubated at 37° C. for 1 h.

(4) Addition of secondary antibody: The enzyme-labeled microtiter-plate was taken out to discard the solution inside, added with the diluted secondary antibody at a concentration of 0.033 μg/ml, covered with the cover film, and incubated at 37° C. for half an hour.

(5) Color development: The enzyme-labeled microtiter-plate was taken out to discard the solution inside, added with the chromogenic solution to develop the color at 25° C. for 13 minutes.

(6) Stop of reaction: The stop solution was added to stop the reaction.

(7) The value was read at 450 nm on a microtiter-plate reader immediately after the addition of the stop solution. The maximum dilution corresponding to the well having an OD value of more than 2.1 times the OD value of the set negative control was determined as the titer of the sample, and the test results are shown in Table 2. NC is a negative control of unimmunized serum, and the initial dilution factor is 1:1,000. The anti-serum after the third immunization was tested. The anti-serum titer of animal No. #1940 was 1:128,000; the anti-serum titer of animal No. #1939 was 1:512,000; the anti-serum titers of the remaining 3 animals (#1941, #1942, #1943) were 1:256,000.

TABLE 2

Test results of serum ELISA after the third immunization:

| Animal No. | Dilution factor | No.1939 | No.1940 | No.1941 | No.1942 | No.1943 |
| --- | --- | --- | --- | --- | --- | --- |
| Negative control | 1:1,000 | 0.087 | 0.090 | 0.093 | 0.143 | 0.101 |
| Dilution 1 | 1:1,000 | 2.798 | 2.350 | 2.404 | 2.546 | 2.706 |
| Dilution 2 | 1:2,000 | 2.607 | 1.980 | 2.036 | 2.147 | 2.339 |
| Dilution 3 | 1:4,000 | 2.557 | 1.750 | 1.970 | 1.830 | 1.986 |
| Dilution 4 | 1:8,000 | 2.264 | 1.473 | 1.522 | 1.381 | 1.463 |
| Dilution 5 | 1:16,000 | 1.908 | 0.956 | 1.105 | 0.953 | 1.024 |
| Dilution 6 | 1:32,000 | 1.453 | 0.754 | 0.725 | 0.595 | 0.659 |
| Dilution 7 | 1:64,000 | 1.071 | 0.427 | 0.513 | 0.366 | 0.407 |
| Dilution 8 | 1:128,000 | 0.625 | 0.274 | 0.278 | 0.216 | 0.261 |
| Dilution 9 | 1:256,000 | 0.368 | 0.138 | 0.194 | 0.164 | 0.175 |

TABLE 2-continued

Test results of serum ELISA after the third immunization:

| Animal No. | Dilution factor | No.1939 | No.1940 | No.1941 | No.1942 | No.1943 |
|---|---|---|---|---|---|---|
| Dilution 10 | 1:512,000 | 0.229 | 0.106 | 0.128 | 0.109 | 0.146 |
| Dilution 11 | Blank control | 0.077 | 0.077 | 0.077 | 0.077 | 0.077 |
|  | Titer | 1:512,000 | 1:128,000 | 1:256,000 | 1:256,000 | 1:256,000 |

2.3 Cell Fusion and Screening of Hybridoma Cell Lines 2.3.1 Cell Fusion:

According to the ELISA test results of Example 2.2, combined with the tissue specificity results, two animals #1942, #1943 were selected for final immunization, and three days later the spleen cells of the two animals were fused with tumor cells. The mouse myeloma cells (SP2/0) and spleen cells were electrofused in a 1:3 ratio and the fused cells were plated into 15 feeder cell plates using HAT medium, and cultured in a $CO_2$ incubator.

2.3.2 Screening of Hybridoma Cell Lines:

After the fused cells were cultured for 7-10 days, the whole medium was replaced and ELISA test was carried out after 4 hours of the medium replacement.

The specific materials and procedures of ELISA were the same as that of ELISA test of animal serum in 2.2.

First ELISA Screening:

There is a total of fifteen 96-well microtiter-plates (from plate No. 41 to plate No. 55). Well 55H12 (well H12 of plate No. 55) was set as positive control, a 1000-fold diluted solution of fused animal serum was added, and the OD value was determined to be 2.215; Well 55G12 (well G12 of plate No. 55) was set as negative control, a blank medium was added, and the OD value was determined to be 0.088. The clones with OD>0.5 were selected.

Second ELISA Screening:

The 68 clones with OD>0.5 of a single-well cell from the first screening were subjected to a second test (same as the above test method). The results are shown in Table 3. 10 clones with an OD of more than 1.0 were selected, namely 41C12, 47A11, 42A3, 42H10, 48D6, 51H10, 52F11, 52H5, 55E9, 55H7.

TABLE 3

Second ELISA screening of hybridoma cells

| 1 | 2 | 3 | 4 | 5 | 6 | 7 | 8 | 9 | 10 | 11 | 12 |
|---|---|---|---|---|---|---|---|---|---|---|---|
| 41C12 | 41F4 | 42A3 | 42D8 | 42H10 | 43B1 | 43B7 | 44D1 | 46A6 | 47A11 | 48B12 | 48D6 |
| 1.942 | 0.748 | 0.966 | 0.660 | 1.254 | 0.524 | 0.638 | 0.540 | 0.629 | 1.102 | 0.791 | 1.362 |
| 50C6 | 51D10 | 51H9 | 51H10 | 51H11 | 52B4 | 52C5 | 52F6 | 52F11 | 52H5 | 52H6 | 53D9 |
| 0.564 | 0.459 | 0.834 | 1.962 | 0.084 | 0.588 | 0.713 | 0.864 | 1.118 | 1.777 | 0.109 | 0.808 |
| 53E2 | 55E9 | 55G5 | 55H2 | 55H7 |  |  |  |  |  | NC | PC |
| 0.558 | 1.294 | 0.757 | 0.716 | 1.148 |  |  |  |  |  | 0.084 | 1.985 |

Third ELISA Screening:

The 10 lines from the second screening were subjected to positive confirmation test (same as the above test method). The experiment results are shown in Table 4. The above 10 cell lines were expanded into a 24-well microtiter-plate, and 2 ml of supernatant of each line was collected for next confirmation step.

TABLE 4

Third ELISA screening of hybridoma cells

| 1 | 2 | 3 | 4 | 5 | 6 | 7 | 8 | 9 | 10 | 11 | 12 |
|---|---|---|---|---|---|---|---|---|---|---|---|
| 41C12 | 47A11 | 42A3 | 42H10 | 48D6 | 51H10 | 52F11 | 52H5 | 55E9 | 55H7 | PC | NC |
| 2.259 | 1.454 | 1.379 | 1.562 | 1.574 | 1.833 | 1.326 | 1.748 | 1.385 | 1.325 | 2.025 | 0.072 |

2.3.3. Cytological Specificity Confirmation

In order to confirm whether these cell lines have specificity to nerve tissues, the supernatants of the third ELISA screening of the 2.3.2 hybridoma cell lines were subjected to immunohistochemical examination. The specific experimental methods were as follows:

negative. These positive clones were selected for a second confirmation and the OD values were confirmed to be relatively higher (see Table 5). These positive monoclones were then expanded into a 24-well microtiter-plate and 2 ml of supernatant of each clone culture was collected for cytological confirmation. It was confirmed by tissue immunochemistry that the clone 51H10 was immunohistochemically positive (FIG. 3).

TABLE 5

Confirmation of second ELISA test of positive subclones

| 42H10E3 | 42H10E4 | 42H10F3 | 42H10G4 | 51H10D9 | 51H10D12 | 51H10E11 | 51H10F8 | 52F11B2 |
|---|---|---|---|---|---|---|---|---|
| 1.566 | 1.579 | 1.544 | 1.592 | 2.188 | 2.254 | 2.154 | 1.601 | 1.616 |
| 52F11H3 | 52F11H6 | 52F11H11 | 55E9A4 | 55E9C6 | 55E9D9 | 55E9E3 | NC | PC |
| 2.158 | 1.488 | 1.504 | 1.485 | 1.348 | 1.439 | 1.542 | 0.073 | 2.034 |

2.3.3.1 Tissue Dehydration Treatment:

The human nerve tissues were taken for dehydration treatment, and the dehydration treatment was carried out by Leica ASP300S. The specific process was as follows:

The tissues was dehydrated with 70%, 85%, 90%, anhydrous ethanol for 30 minutes, respectively; then dehydrated twice with anhydrous ethanol for 60 minutes each time; then treated with clearing agent for 30 minutes, then treated with clearing agent twice for 60 minutes each time; and then treated 3 times with paraffin, for 60 minutes, 120 minutes and 180 minutes, respectively, and then subjected to embedding operation using a Leica EG1150 embedding machine, to prepare a wax block, which was cut into sections with a thickness of 4 µm.

2.3.3.2 In Situ Hybridization:

The nerve tissue sections were baked at 85° C. for 20 min; treated 3 times with a dewaxing agent for 1 minute each time; dewaxed 3 times with anhydrous alcohol for 1 minute each time; washed 3 times with water for 1 minute each time; thermal repaired with ER2 (pH=9 buffer solution) for 20 minutes, cooled for 12 minutes, then washed 3 times with water for 1 minute each time; then blocked for 30 minutes; washed 3 times with water for 1 minute each time; added with the supernatant of the cell line and incubated for 30 minutes, washed 3 times with water for 1 minute each time; incubated for 8 minutes with an enhancing agent, washed 3 times with water for 2 minutes each time, added with the secondary antibody and incubated for 8 minutes; washed 3 times with water for 2 minutes each time; developed color with DAB for 8 minutes; washed 3 times with water for 1 minute each time, stained with hematoxylin for 10 minutes; washed 3 times with water for 1 minute each time, dehydrated with alcohol, air-dried and sealed. Observations were performed using an Olympus optical microscope.

It was observed by optical microscopy that the specificity and hybridization signals of the antibodies secreted by cell lines 42H10, 51H10, 52F11, 55E9 in neural tissues met the requirements.

2.3.4 Subcloning

According to the results of the cytology test of Example 2.3.3, 42H10, 51H10, 52F11, 55E9 were selected for subcloning. The four cell lines were subcloned by limiting dilution method. The four cell lines were plated into a 96-well feeder cell plate. After 7-10 days of culture, 12 monoclones were selected from each line for ELISA test (same as above test method). The results showed that 16 clones such as 42H10E3, 42H10E4, 42H10F3, 42H10G4, 51H10D9, 51H10D12, 51H10E11, 51H10F8, 52F11B2, 52F11H3, 52F11H6, 52F11H11, 55E9A4, 55E9C6, 55E9D9, and 55E9E3 were positive and the others were 51H10D9, 51H10D12, and 51H10F8 were selected for the second subcloning (subcloning method was the same as above). After 7-10 days of culture, 12 monoclonal wells were selected for ELISA test. The results showed that they were all positive, indicating that these were homozygous monoclones. Five sub-clones were randomly selected, and the supernatants were subjected to titer assay and subtype identification (Southern Biotech kit, Cat. No. ST17). The experimental results showed that the OD values of the five clones were identical, the titer was 1:2400 and the subtypes were IgG2b, K. Finally, 51H10D12 was selected for cell cryopreservation.

Example 3 [Antibody Sequencing]

In order to determine the monoclonal antibody sequence, one monoclone 51H10D12 was selected for sequencing. Total RNA was isolated from hybridoma cells according to the technical manual of TRIzol reagent. The total RNA was then reverse transcribed into cDNA using isotype-specific antisense primers or universal primers, according to the PrimeScript™ First Strand cDNA Synthesis Kit Technical Manual. Antibody fragments of VH and VL were amplified according to the standard operating procedure (SOP) method of rapid amplification of cDNA ends (RACE) of GenScript. The amplified antibody fragments were cloned into standard cloning vectors, respectively. Colony PCR was performed to screen for clones containing inserts of the correct size. At least 5 colonies with the correct size inserts were sequenced. The sequences of the different clones were aligned to determine the consensus sequence of these clones.

The DNA sequence of VH is thus determined as shown in SEQ ID NO:10; the DNA sequence of VL is determined as shown in SEQ ID NO:11.

```
Leader sequence-FR1-CDR1-FR2-CDR2-FR3-
CDR3-FR4-constant region-stop codon
ATGGGATGGAGCTCTATCATCCTCTTCTTGGTAGCAACAGCTACAGGTGT
CCACTCCCAGGTCCAAC Leader sequence
TGCAGCAGCCTGGGGCTGAGCTGGTGAGGCCTGGAGCTTCAGTGAAGCTG
TCCTGCAAGGCTTCTGG
CTACTCCTTCACCAGTTACTGGATGAACTGGGTGAAGCAGAGGCCTGGAC
AAGGCCTTGAGTGGATT

CDR1
GGCATGATTCATCCTTCCGATAGTGAAACTAGGTTAAATCAGAAGTTCAA
GGACAAGGCCACATTGA
```

```
CDR2
CTGTAGACAAATCCTCCAGCACAGCCTACATGCAACTCAGCAGCCCGACA
TCTGAGGACTCTGCGGT
CTATTACTGTGCAAGACAAGGGTTTGCTTACTGGGGCCAAGGGACTCTGG
TCACTGTCTCTACAGCC

CDR3
AAAACAACACCCCCATCAGTCTATCCACTGGCCCCTGGGTGTGGAGATAC
AACTGGTTCCTCCGTGA

Constant region
                                        (SEQ ID NO: 10)
CTCTGGGATGCCTGGTCAAGGGCTACTTCCCTGAGTCAGTGACTGTGACT
TGGAACTCTGGATCCCT
GTCCAGCAGTGTGCACACCTTCCCAGCTCTCCTGCAGTCTGGACTCTACAC
TATGAGCAGCTCAGTG
ACTGTCCCCTCCAGCACCTGGCCAAGTCAGACCGTCACCTGCAGCGTTGC
TCACCCAGCCAGCAGCA
CCACGGTGGACAAAAAACTTGAGCCCAGCGGGCCCATTTCAACAATCAA
CCCCTGTCCTCCATGCAA
GGAGTGTCACAAATGCCCAGCTCCTAACCTCGAGGGTGGACCATCCGTCT
TCATCTTCCCTCCAAAT
ATCAAGGATGTACTCATGATCTCCCTGACACCCAAGGTCACGTGTGTGGT
GGTGGATGTGAGCGAGG
ATGACCCAGACGTCCAGATCAGCTGGTTTGTGAACAACGTGGAAGTACAC
ACAGCTCAGACACAAAC
CCATAGAGAGGATTACAACAGTACTATCCGGGTGGTCAGCACCCTCCCCA
TCCAGCACCAGGACTGG
ATGAGTGGCAAGGAGTTCAAATGCAAGGTCAACAACAAAGACCTCCCAT
CACCCATCGAGAGAACCA
TCTCAAAAATTAAAGGGCTAGTCAGAGCTCCACAAGTATACATCTTGCCG
CCACCAGCAGAGCAGTT
GTCCAGGAAAGATGTCAGTCTCACTTGCCTGGTCGTGGGCTTCAACCCTG
GAGACATCAGTGTGGAG
TGGACCAGCAATGGGCATACAGAGGAGAACTACAAGGACACCGCACCAG
TCCTGGACTCTGACGGTT
CTTACTTCATATATAGCAAGCTCAATATGAAAACAAGCAAGTGGGAGAA
AACAGATTCCTTCTCATG
CAACGTGAGACACGAGGGTCTGAAAAATTACTACCTGAAGAAGACCATC
TCCCGGTCTCCGGGTAAA
TGA Leader sequence-FR1-CDR1-FR2-CDR2-FR3-CDR3-FR4-
constant region-stop codon
ATGAGGGTCCTTGCTGAGCTCCTGGGGCTGCTGCTGTTCTGCTTTTTAGGT
GTGAGATGTGACATCC Leader sequence
AGATGAACCAGTCTCCATCCAGTCTGTCTGCATCCCTTGGAGACACAATT
ACCATCACTTGCCATGC
CAGTCAGAACATTAATGTTTGGTTAAGCTGGTACCAGCAGAAACCAGGAA
ATATTCCTAAACTATTG

CDR 1
ATCTATAAGGCTTCCAACTTGCGCACAGGCGTCCCATCAAGGTTTAGTGG
CAGTGGATCTGGAACAG

CDR2
GTTTCACATTAACCATCAGCAGCCTGCAGCCTGAAGACATTGCCACTTAC
TACTGTCACCAGGGTCA
AAGTTATCCGTGGACGTTCGGTGGAGGCACCAAGCTGGAAATCAAACGG
GCTGATGCTGCACCAACT

CDR3
GTATCCATCTTCCCACCATCCAGTGAGCAGTTAACATCTGGAGGTGCCTC
AGTCGTGTGCTTCTTGA

Constant region
                                        (SEQ ID NO: 11)
ACAACTTCTACCCCAAAGACATCAATGTCAAGTGGAAGATTGATGGCAGT
GAACGACAAAATGGCGT
CCTGAACAGTTGGACTGATCAGGACAGCAAAGACAGCACCTACAGCATG
AGCAGCACCCTCACGTTG
ACCAAGGACGAGTATGAACGACATAACAGCTATACCTGTGAGGCCACTC
ACAAGACATCAACTTCAC
CCATTGTCAAGAGCTTCAACAGGAATGAGTGTTAG
```

The amino acid sequences of VH and VL can be deduced from their DNA sequences. The amino acid sequence of VH is as shown in SEQ ID NO:7, and the amino acid sequence of VL is as shown in SEQ ID NO:8.

```
Leader sequence-FR1-CDR1-FR2-CDR2-FR3-CDR3-FR4-
constant region
                                        (SEQ ID NO: 7)
MGWSSIILFLVATATGVHSQVQLQQPGAELVRPGASVKLSCKASGYSFT
SYWMNWVKQRPGQGLEWI Leader sequence
CDR1
GMIHPSDSETRLNQKFKDKATLTVDKSSSTAYMQLSSPTSEDSAVYYCAR
QGFAYWGQGTLVTVSTA

CDR2
CDR3
KTTPPSVYPLAPGCGDTTGSSVTLGCLVKGYFPESVTVTWNSGSLSSSVH
TFPALLQSGLYTMSSSV

Constant region
TVPSSTWPSQTVTCSVAHPASSTTVDKKLEPSGPISTINPCPPCKECHK
CPAPNLEGGPSVFIFPPN
IKDVLMISLTPKVTCVVVDVSEDDPDVQISWFVNNVEVHTAQTQTHRE
DYNSTIRVVSTLPIQHQDW
MSGKEFKCKVNNKDLPSPIERTISKIKGLVRAPQVYILPPPAEQLSRKDV
SLTCLVVGFNPGDISVE
WTSNGHTEENYKDTAPVLDSDGSYFIYSKLNMKTSKWEKTDSFSCNVRH
EGLKNYYLKKTISRSPGK Leader sequence-FR1-CDR1-FR2-CDR2-FR3-CDR3-FR4-
constant region
                                        (SEQ ID NO: 8)
MRVLAELLGLLLFCFLGVRCDIQMNQSPSSLSASLGDTITITCHASQNI
NVWLSWYQQKPGNIPKLL Leader sequence
CDR1
IYKASNLRTGVPSRFSGSGSGTGFTLTISSLQPEDIATYYCHQGQSYPWT
FGGGTKLEIKRADAAPT

CDR2
CDR3
VSIFPPSSEQLTSGGASVVCFLNNFYPKDINVKWKIDGSERQNGVLNS
WTDQDSKDSTYSMSSTLTL

Constant region
TKDEYERHNSYTCEATHKTSTSPIVKSFNRNEC
```

It can be deduced that the RNA sequence encoding VH is as shown in SEQ ID NO:12, and the RNA sequence encoding VL is as shown in SEQ ID NO:13.

Example 4 [Specificity Test of Antibody]

4.1 Preparation of hNav1.9 Antigen

The human Nav1.9-HA plasmid (7-8 µg) was transfected into ND7/23 cells (10 cm cell dishes), cultured at 37° C. for 10 hours, and then cultured in a cell dish at 29° C. for 20 hours to collect the cells.

4.2 Western Blotting Analysis

1. The cell culture medium was aspirated, 2 ml of sterilized PBS was added and the cell dish was gently rotated to wash the cells twice.

2. 1 ml of Western and IP cell lysate were added, and the cells were collected by cell scraper and lysed on ice for half an hour.

3. A sonicator was used for ultrasonically disruption twice for 3s each time.

4. The cell lysate was centrifuged at 12000 rpm for 10 minutes at 4° C. to collect the cell lysis supernatant.

5. 40 µl of the supernatant of the cell lysate was taken and electrophoresed on an 8% SDS-polyacrylamide gel.

6. After transformation, the cells were incubated with HA tag (1:2000) antibody and 51H10D12 (1:300) antibody for 1 hour at room temperature.

7. The cells were washed three times with PBS for 5 minutes each time;

8. A digoxigenin-labeled anti-mouse antibody (1:20000) was added and incubated for 1 hour at room temperature;

9. The cells were washed three times with PBS for 5 minutes each time;

10. A digoxin substrate was added and developed for 5-10 minutes.

11. Western blot hybridization was performed.

4.3 Western Hybridization Results

As shown in FIG. 4, the antibody 51H10D12 and the HA tag can produce a hybridization signal between 130-250 KD and no corresponding signal was detected in the negative control, the hybridization signal was close to the molecular weight of hNav1.9 of about 210 kDa, indicating that the antibody can recognize the protein of hNav1.9.

Example 5 [Analgesic Efficacy of 51H10D12 Antibody in Wild-Type Mice]

In order to test whether the antibody 51H10D12 has an analgesic effect, we used Formalin inflammatory pain model to evaluate the efficacy of the antibody. After intravenous injection of the antibody, 2 µl of 5% formalin was injected to the mice hind paw after 30 minutes injection of the antibody. The time of paw licking and withdrawal was recorded every 5 minutes, to evaluate the analgesic efficacy of different treatments on Formalin-induced spontaneous inflammatory pain.

5.1 Experimental Steps

According to the method of Lee et al. (2014, Cell 157, 1393-1404), 12 wild-type mice were tested after 2 days of adaptation. They were randomly divided into 2 groups, one served as control group, injected with PBS by tail vein, and the other served as experimental group, injected with 10 mg/kg of antibody 51H10D12 by tail vein. After half an hour, 20 µL of 5% Formalin was injected subcutaneously into the hind paw to produce pain caused by acute inflammation, and the time of paw licking and withdrawal was recorded within every 5 minutes for a total of 45 minutes. Phase I (0-10 minutes) and phase II (10-45 minutes) were statistically analyzed, respectively. Phase I represented acute pain, and phase II represented spontaneous persistent pain. After the experiment, the two phases as well as the differences between the drug injection group and the control group during various phases in the wild-type mice were statistically analyzed.

5.2 Experimental Results

As shown in FIG. 5, the wild-type mice were injected with antibody 51H10D12 by tail vein, and given 5% Formalin to induce acute inflammatory pain. The antibody can reduce the total time of paw licking within 10-15 minutes and 30-35 minutes after subcutaneous injection of 5% Formalin by hind paw, namely, the total time of paw licking in Phase II, which was significantly different compared to that of the negative control. The results showed that antibody 51H10D12 can alleviate phase II inflammatory pain induced by 5% Formalin in wild type mice, which is equivalent to the effect reported in the literature.

```
Sequence listing:
                                             (SEQ ID NO: 1)
SYWMN (SEQ ID NO: 2)
MIHPSDSETRLNQKFKD (SEQ ID NO: 3)
QGFAY (SEQ ID NO: 4)
HASQNINVWLS (SEQ ID NO: 5)
KASNLRT (SEQ ID NO: 6)
HQGQSYPWT (SEQ ID NO: 7)
MGWSSIILFLVATATGVHSQVQLQQPGAELVRPGASVKLSCKASGYSF

TSYWMNWVKQRPGQGLEWIGMIHPSDSETRLNQKFKDKATLTVDKSSS

TAYMQLSSPTSEDSAVYYCARQGFAYWGQGTLVTVSTAKTTPPSVYPL

APGCGDTTGSSVTLGCLVKGYFPESVTVTWNSGSLSSSVHTFPALLQS

GLYTMSSSVTVPSSTWPSQTVTCSVAHPASSTTVDKKLEPSGPISTIN

PCPPCKECHKCPAPNLEGGPSVFIFPPNIKDVLMISLTPKVTCVVVDV

SEDDPDVQISWFVNNVEVHTAQTQTHREDYNSTIRVVSTLPIQHQDWM

SGKEFKCKVNNKDLPSPIERTISKIKGLVRAPQVYILPPPAEQLSRKD

VSLTCLVVGFNPGDISVEWTSNGHTEENYKDTAPVLDSDGSYFIYSKL

NMKTSKWEKTDSFSCNVRHEGLKNYYLKKTISRSPGK (SEQ ID NO: 8)
MRVLAELLGLLLFCFLGVRCDIQMNQSPSSLSASLGDTITITCHASQN

INVWLSWYQQKPGNIPKLLIYKASNLRTGVPSRFSGSGSGTGFTLTIS

SLQPEDIATYYCHQGQSYPWTFGGGTKLEIKRADAAPTVSIFPPSSEQ

LTSGGASVVCFLNNFYPKDINVKWKIDGSERQNGVLNSWTDQDSKDST

YSMSSTLTLTKDEYERHNSYTCEATHKTSTSPIVKSFNRNEC
```

(SEQ ID NO: 9)
DVEFSGEDNAQRIT (SEQ ID NO: 10)
ATGGGATGGAGCTCTATCATCCTCTTCTTGGTAGCAACAGCTACAGGT

GTCCACTCCCAGGTCCAACTGCAGCAGCCTGGGGCTGAGCTGGTGAGG

CCTGGAGCTTCAGTGAAGCTGTCCTGCAAGGCTTCTGGCTACTCCTTC

ACCAGTTACTGGATGAACTGGGTGAAGCAGAGGCCTGGACAAGGCCTT

GAGTGGATTGGCATGATTCATCCTTCCGATAGTGAAACTAGGTTAAAT

CAGAAGTTCAAGGACAAGGCCACATTGACTGTAGACAAATCCTCCAGC

ACAGCCTACATGCAACTCAGCAGCCCGACATCTGAGGACTCTGCGGTC

TATTACTGTGCAAGACAAGGGTTTGCTTACTGGGGCCAAGGGACTCTG

GTCACTGTCTCTACAGCCAAAACAACACCCCCATCAGTCTATCCACTG

GCCCCTGGGTGTGGAGATACAACTGGTTCCTCCGTGACTCTGGGATGC

CTGGTCAAGGGCTACTTCCCTGAGTCAGTGACTGTGACTTGGAACTCT

GGATCCCTGTCCAGCAGTGTGCACACCTTCCCAGCTCTCCTGCAGTCT

GGACTCTACACTATGAGCAGCTCAGTGACTGTCCCCTCCAGCACCTGG

CCAAGTCAGACCGTCACCTGCAGCGTTGCTCACCCAGCCAGCAGCACC

ACGGTGGACAAAAAACTTGAGCCCAGCGGGCCCATTTCAACAATCAAC

CCCTGTCCTCCATGCAAGGAGTGTCACAAATGCCCAGCTCCTAACCTC

GAGGGTGGACCATCCGTCTTCATCTTCCCTCCAAATATCAAGGATGTA

CTCATGATCTCCCTGACACCCAAGGTCACGTGTGTGGTGGTGGATGTG

AGCGAGGATGACCCAGACGTCCAGATCAGCTGGTTTGTGAACAACGTG

GAAGTACACACAGCTCAGACACAAACCCATAGAGAGGATTACAACAGT

ACTATCCGGGTGGTCAGCACCCTCCCCATCCAGCACCAGGACTGGATG

AGTGGCAAGGAGTTCAAATGCAAGGTCAACAACAAAGACCTCCCATCA

CCCATCGAGAGAACCATCTCAAAAATTAAAGGGCTAGTCAGAGCTCCA

CAAGTATACATCTTGCCGCCACCAGCAGAGCAGTTGTCCAGGAAAGAT

GTCAGTCTCACTTGCCTGGTCGTGGGCTTCAACCCTGGAGACATCAGT

GTGGAGTGGACCAGCAATGGGCATACAGAGGAGAACTACAAGGACACC

GCACCAGTCCTGGACTCTGACGGTTCTTACTTCATATATAGCAAGCTC

AATATGAAAACAAGCAAGTGGGAGAAAACAGATTCCTTCTCATGCAAC

GTGAGACACGAGGGTCTGAAAAATTACTACCTGAAGAAGACCATCTCC

CGGTCTCCGGGTAAATGA (SEQ ID NO: 11)
ATGAGGGTCCTTGCTGAGCTCCTGGGGCTGCTGCTGTTCTGCTTTTTA

GGTGTGAGATGTGACATCCAGATGAACCAGTCTCCATCCAGTCTGTCT

GCATCCCTTGGAGACACAATTACCATCACTTGCCATGCCAGTCAGAAC

ATTAATGTTTGGTTAAGCTGGTACCAGCAGAAACCAGGAAATATTCCT

AAACTATTGATCTATAAGGCTTCCAACTTGCGCACAGGCGTCCCATCA

AGGTTTAGTGGCAGTGGATCTGGAACAGGTTTCACATTAACCATCAGC

AGCCTGCAGCCTGAAGACATTGCCACTTACTACTGTCACCAGGGTCAA

AGTTATCCGTGGACGTTCGGTGGAGGCACCAAGCTGGAAATCAAACGG

GCTGATGCTGCACCAACTGTATCCATCTTCCCACCATCCAGTGAGCAG

TTAACATCTGGAGGTGCCTCAGTCGTGTGCTTCTTGAACAACTTCTAC

CCCAAAGACATCAATGTCAAGTGGAAGATTGATGGCAGTGAACGACAA

AATGGCGTCCTGAACAGTTGGACTGATCAGGACAGCAAAGACAGCACC

TACAGCATGAGCAGCACCCTCACGTTGACCAAGGACGAGTATGAACGA

CATAACAGCTATACCTGTGAGGCCACTCACAAGACATCAACTTCACCA

TTGTCAAGAGCTTCAACAGGAATGAGTGTTAG (SEQ ID NO: 12)
AUGGGAUGGAGCUCUAUCAUCCUCUUCUUGGUAGCAACAGCUACAGGU

GUCCACUCCCAGGUCCAACUGCAGCAGCCUGGGGCUGAGCUGGUGAGG

CCUGGAGCUUCAGUGAAGCUGUCCUGCAAGGCUUCUGGCUACUCCUUC

ACCAGUUACUGGAUGAACUGGGUGAAGCAGAGGCCUGGACAAGGCCUU

GAGUGGAUUGGCAUGAUUCAUCCUUCCGAUAGUGAAACUAGGUUAAAU

CAGAAGUUCAAGGACAAGGCCACAUUGACUGUAGACAAAUCCUCCAGC

ACAGCCUACAUGCAACUCAGCAGCCCGACAUCUGAGGACUCUGCGGUC

UAUUACUGUGCAAGACAAGGGUUUGCUUACUGGGGCCAAGGGACUCUG

GUCACUGUCUCUACAGCCAAAACAACACCCCCAUCAGUCUAUCCACUG

GCCCCUGGGUGUGGAGAUACAACUGGUUCCUCCGUGACUCUGGGAUGC

CUGGUCAAGGGCUACUUCCCUGAGUCAGUGACUGUGACUUGGAACUCU

GGAUCCCUGUCCAGCAGUGUGCACACCUUCCCAGCUCUCCUGCAGUCU

GGACUCUACACUAUGAGCAGCUCAGUGACUGUCCCCUCCAGCACCUGG

CCAAGUCAGACCGUCACCUGCAGCGUUGCUCACCCAGCCAGCAGCACC

ACGGUGGACAAAAAACUUGAGCCCAGCGGGCCCAUUUCAACAAUCAAC

CCCUGUCCUCCAUGCAAGGAGUGUCACAAAUGCCCAGCUCCUAACCUC

GAGGGUGGACCAUCCGUCUUCAUCUUCCCUCCAAAUAUCAAGGAUGUA

CUCAUGAUCUCCCUGACACCCAAGGUCACGUGUGUGGUGGUGGAUGUG

AGCGAGGAUGACCCAGACGUCCAGAUCAGCUGGUUUGUGAACAACGUG

GAAGUACACACAGCUCAGACACAAACCCAUAGAGAGGAUUACAACAGU

ACUAUCCGGGUGGUCAGCACCCUCCCCAUCCAGCACCAGGACUGGAUG

AGUGGCAAGGAGUUCAAAUGCAAGGUCAACAACAAAGACCUCCCAUCA

CCCAUCGAGAGAACCAUCUCAAAAAUUAAAGGGCUAGUCAGAGCUCCA

CAAGUAUACAUCUUGCCGCCACCAGCAGAGCAGUUGUCCAGGAAAGAU

GUCAGUCUCACUUGCCUGGUCGUGGGCUUCAACCCUGGAGACAUCAGU

GUGGAGUGGACCAGCAAUGGGCAUACAGAGGAGAACUACAAGGACACC

GCACCAGUCCUGGACUCUGACGGUUCUUACUUCAUAUAUAGCAAGCUC

AAUAUGAAAACAAGCAAGUGGGAGAAAACAGAUUCCUUCUCAUGCAAC

GUGAGACACGAGGGUCUGAAAAAUUACUACCUGAAGAAGACCAUCUCC

CGGUCUCCGGGUAAAUGA (SEQ ID NO: 13)
AUGAGGGUCCUUGCUGAGCUCCUGGGGCUGCUGCUGUUCUGCUUUUUA

GGUGUGAGAUGUGACAUCCAGAUGAACCAGUCUCCAUCCAGUCUGUCU

GCAUCCCUUGGAGACACAAUUACCAUCACUUGCCAUGCCAGUCAGAAC

AUUAAUGUUUGGUUAAGCUGGUACCAGCAGAAACCAGGAAAUAUUCCU

AAACUAUUGAUCUAUAAGGCUUCCAACUUGCGCACAGGCGUCCCAUCA

AGGUUUAGUGGCAGUGGAUCUGGAACAGGUUUCACAUUAACCAUCAGC

AGCCUGCAGCCUGAAGACAUUGCCACUUACUACUGUCACCAGGGUCAA

AGUUAUCCGUGGACGUUCGGUGGAGGCACCAAGCUGGAAAUCAAACGG

GCUGAUGCUGCACCAACUGUAUCCAUCUUCCCACCAUCCAGUGAGCAG

UUAACAUCUGGAGGUGCCUCAGUCGUGUGCUUCUUGAACAACUUCUAC

CCCAAAGACAUCAAUGUCAAGUGGAAGAUUGAUGGCAGUGAACGACAA

AAUGGCGUCCUGAACAGUUGGACUGAUCAGGACAGCAAAGACAGCACC

UACAGCAUGAGCAGCACCCUCACGUUGACCAAGGACGAGUAUGAACGA

CAUAACAGCUAUACCUGUGAGGCCACUCACAAGACAUCAACUUCACCC

AUUGUCAAGAGCUUCAACAGGAAUGAGUGUUAG

---

What is claimed is:

1. An antibody or an antigen binding fragment thereof that specifically binds to a cytomembrane voltage-gated sodium ion channel a subunit Nav1.9,
   wherein the heavy chain variable region of the antibody or antigen binding fragment thereof comprises CDR sequences of CDRH1 as shown in SEQ ID NO:1, CDRH2 as shown in SEQ ID NO:2 and CDRH3 as shown in SEQ ID NO:3; and
   the light chain variable region of the antibody or antigen binding fragment thereof comprises CDR sequences of CDRL1 as shown in SEQ ID NO:4, CDRL2 as shown in SEQ ID NO:5, and CDRL3 as shown in SEQ ID NO:6.

2. The antibody or antigen binding fragment thereof according to claim 1, wherein the antibody or antigen binding fragment comprises a heavy chain variable region as shown in SEQ ID NO:7 and/or a light chain variable region as shown in SEQ ID NO:8.

3. The antibody or antigen binding fragment thereof according to claim 1, wherein the antibody further comprises an antibody constant region.

4. The antibody or antigen binding fragment thereof according to claim 1, wherein the antibody or antigen binding fragment is in a structural form selected from the group consisting of a full antibody, Fab, F(ab')2, dsFv, scFv, a diabody, a minibody, a bispecific antibody, a multispecific antibody, a chimeric antibody, and a CDR-grafted antibody.

5. The antibody or antigen binding fragment thereof according to claim 1, wherein the antibody is a monoclonal antibody.

6. The antibody or antigen binding fragment thereof according to claim 5, wherein the antibody is a humanized antibody.

7. The antibody or antigen binding fragment thereof according to claim 1,
   wherein the heavy chain variable region of the antibody or antigen binding fragment thereof comprises an antigen binding region consisting of the CDR sequences of CDRH1 as shown in SEQ ID NO:1, CDRH2 as shown in SEQ ID NO:2 and CDRH3 as shown in SEQ ID NO:3; and the light chain variable region of the antibody or antigen binding fragment thereof comprises an antigen binding region consisting of CDR sequences of CDRL1 as shown in SEQ ID NO:4, CDRL2 as shown in SEQ ID NO:5, and CDRL3 as shown in SEQ ID NO:6.

8. A pharmaceutical composition comprising the antibody or antigen binding fragment thereof of claim 1, and a pharmaceutically acceptable carrier.

\* \* \* \* \*